United States Patent
Hull et al.

(10) Patent No.: US 10,422,769 B2
(45) Date of Patent: Sep. 24, 2019

(54) MAGNETIC CHARACTERIZATION OF BOND STRENGTH

(71) Applicant: The Boeing Company, Chicago, IL (US)

(72) Inventors: John R. Hull, Sammamish, WA (US); Robert J. Miller, Fall City, WA (US)

(73) Assignee: The Boeing Company, Chicago, IL (US)

( * ) Notice: Subject to any disclaimer, the term of this patent is extended or adjusted under 35 U.S.C. 154(b) by 525 days.

(21) Appl. No.: 14/742,354

(22) Filed: Jun. 17, 2015

(65) Prior Publication Data

US 2016/0370322 A1 Dec. 22, 2016

(51) Int. Cl.
| | |
|---|---|
| *G01N 27/72* | (2006.01) |
| *B23B 5/26* | (2006.01) |
| *B23B 7/12* | (2006.01) |
| *B23B 27/06* | (2006.01) |
| *B23B 27/08* | (2006.01) |
| *B23B 27/12* | (2006.01) |
| *G01N 1/00* | (2006.01) |
| *B32B 7/12* | (2006.01) |
| *B32B 27/06* | (2006.01) |
| *B32B 5/26* | (2006.01) |
| *B32B 27/08* | (2006.01) |
| *B32B 27/12* | (2006.01) |

(52) U.S. Cl.
CPC ............... *G01N 27/72* (2013.01); *B32B 5/26* (2013.01); *B32B 7/12* (2013.01); *B32B 27/06* (2013.01); *B32B 27/08* (2013.01); *B32B 27/12* (2013.01); *G01N 1/00* (2013.01); *G01N 27/725* (2013.01); *B32B 2307/50* (2013.01)

(58) Field of Classification Search
USPC ........................................ 73/150 A
See application file for complete search history.

(56) References Cited

U.S. PATENT DOCUMENTS

| | | | | |
|---|---|---|---|---|
| 5,640,088 | A * | 6/1997 | Sasahara | G01N 27/72 324/209 |
| 5,902,935 | A | 5/1999 | Georgeson | |
| 6,535,824 | B1 * | 3/2003 | Mansky | B01J 19/0046 374/49 |
| 6,586,930 | B1 * | 7/2003 | Kumar | G01B 7/10 324/225 |
| 6,675,112 | B1 * | 1/2004 | Chadwick | G01N 3/32 702/56 |

(Continued)

OTHER PUBLICATIONS

Carpenter Technology Corporation. "Carpenter HyMu "80"® Alloy" Datasheet. Published Jul. 30, 2010. Accessed Dec. 7, 2018. https://www.spacematdb.com/spacemat/manudatasheets/hyNu80.pdf.*

*Primary Examiner* — Justin Seo
*Assistant Examiner* — Jean F Morello
(74) *Attorney, Agent, or Firm* — Miller, Matthias & Hull LLP (57) ABSTRACT

A tester for bonded composite materials uses a magnetic source to generate a response signal from wires infused in an adhesive used between layers of the composite material. Acoustic or magnetic response signals, separately or in combination, can be received and analyzed to detect stresses in wires indicative of voids in the adhesive or other defects affecting the bond quality between layers of the composite material.

21 Claims, 9 Drawing Sheets

(56) References Cited

U.S. PATENT DOCUMENTS

| | | | |
|---|---|---|---|
| 8,343,298 B2 * | 1/2013 | Rawlings | B29C 65/8284 156/272.2 |
| 8,486,545 B2 | 7/2013 | Lanning | |
| 8,527,218 B2 | 9/2013 | Georgeson | |
| 2010/0005896 A1 * | 1/2010 | Miller | B29C 65/8284 73/779 |
| 2011/0118994 A1 | 5/2011 | Georgeson | |
| 2015/0128709 A1 * | 5/2015 | Stewart | G01N 29/11 73/588 |

* cited by examiner

MAGNETIC CHARACTERIZATION OF BOND STRENGTH

FIELD

This disclosure relates to layered composite materials and more particularly to characterizing bond strength in a layered composite material.

BACKGROUND

The joining of plastic parts to each other, either with or without reinforcing fibers in the parts, is a common and important procedure in many manufacturing processes. In general, once these bonds are formed, it is difficult to measure the bond strength non-destructively. The most common way to test the strength of a bond joint is to pull with some prescribed force on the two pieces that are bonded together to see if they come apart. In many manufactured assemblies, this is impractical, as the pieces that are bonded may be difficult to reach. Special samples can be made to test the procedure forming the bond, but such test methods do not test the actual manufactured part. The ability to determine the integrity of such bonds would have great impact in the design of machinery. For example, assurance of a robust bond between plastic parts could eliminate the need for mechanical fasteners in a number of structures.

SUMMARY

In an aspect of the disclosure, a composite material may include layers of material co-bonded with an adhesive incorporating a plurality of wires. A method for non-destructive determination of an as-cured bond strength of the composite material includes exposing the composite material to a magnetic field, monitoring for a response signal from one or more of the plurality of wires resulting from exposure to the magnetic field, and determining a quality of the as-cured bond strength of the composite material based on the response signal.

In another aspect of the disclosure, a test apparatus may be used for non-destructive determination of an as-cured adhesive bond strength of a composite material that includes layers of material co-bonded with an adhesive. The adhesive may include a plurality of ferro-magnetic wires. The test apparatus may include a signal source positioned proximate the composite material, the signal source transmitting a primary signal into the composite material. The test apparatus may also include a detector positioned proximate the composite material. The detector may receive a response signal generated by at least one wire of the plurality of wires responsive to the primary signal. The test apparatus may also include an analyzer that receives the response signal and determines a presence of a defect in a bond between the adhesive and a layer of the composite material based on a characteristic of the response signal.

In yet another aspect of the disclosure, a method of manufacturing and testing a composite material includes disposing a plurality of wires in an adhesive and bonding the layers of material using the adhesive to form the composite material. Each of the plurality of wires may be ferromagnetic and magnetostrictive. The method may continue by exposing the composite material to a primary signal via a signal source disposed proximate the composite material and then receiving a response signal from one or more of the plurality of wires responsive to the primary signal. The method may conclude by determining a quality of an as-cured adhesive bond using a ratio of a first harmonic of the response signal and a third harmonic of the response signal.

In still another aspect of the disclosure, a composite material may include a first layer of material and a second layer of material and an adhesive disposed between the first layer of material and the second layer of material that bonds the first and second layers of material. The adhesive may include a plurality of individual wires. Each of the plurality of individual wires may be ferro-magnetic and magnetostrictive. The plurality of individual wires may each be oriented in substantially the same direction.

The features, functions, and advantages that have been discussed can be achieved independently in various embodiments or may be combined in yet other embodiments further details of which can be seen with reference to the following description and drawings.

BRIEF DESCRIPTION OF THE DRAWINGS

For a more complete understanding of the disclosed methods and apparatuses, reference should be made to the embodiment illustrated in greater detail on the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

Bond strength in a composite material is vitally important when the composite material is used in many applications, including but not limited to, aeronautical and aerospace applications. Bond strength is a function of the adhesion of adjacent layers of the composite material to an adhesive disposed between these adjacent layers. For example, one defect in a composite material that contributes to weak bonds is a gap or void where an area between the layers simply has no adhesive. Large areas of such a defect can be detected by ultrasound, but smaller areas, on the order of ¼ inch or about 6 mm in diameter, more or less, can be difficult to identify. An additional defect of concern is when the adhesive is evenly spread without voids but there is no adhesion with at least one of the surfaces due to contamination such as by an oil spot on one surface.

A characteristic of some ferro-magnetic materials may be used to identify these defects. These ferro-magnetic materials respond to a magnetic field (an H field) by developing a corresponding response magnetic field when exposed to the stimulation (a B field) that reaches a saturation level at high field strengths and lags the H field in a relationship determined by the coercivity of the ferro-magnetic material. In addition, some of these ferro-magnetic materials also may change their physical shape when exposed to a magnetic field, a property known as magnetostriction. When a frequency of the magnetic field is in an audio range, this change in physical size can cause an audible response. To illustrate, many electric power transformers hum at 60 Hz as a result of magnetostriction during operation.

Wires with suitable magnetic properties, often including magnetostrictive properties as well, may be mixed into an adhesive and disposed with the adhesive between the layers of the composite material. In an embodiment, the wires may have a length approximately the same size as the bonding defects of interest. In an embodiment, these wires may be 2-8 millimeters in length. Curing of the adhesive, usually at a high temperature, results in a residual thermal stress once the bond is cured and returned to an ambient temperature. The wires embedded within the adhesive that are near void boundaries, that cross void boundaries, or are located at a point where the adhesive is not fully attached to both adjacent layers of the composite material will have a different residual stress compared to wires in those locations with well-formed bonds.

By exposing these wires to an alternating magnetic field, each area with a defect-free bond will react magnetically and acoustically in one fashion, while those areas with defects, where the wires experience higher stresses, will react differently. These differences in magnetic and/or acoustic response can be compared to identify areas with defective bonding.

Figure 1:
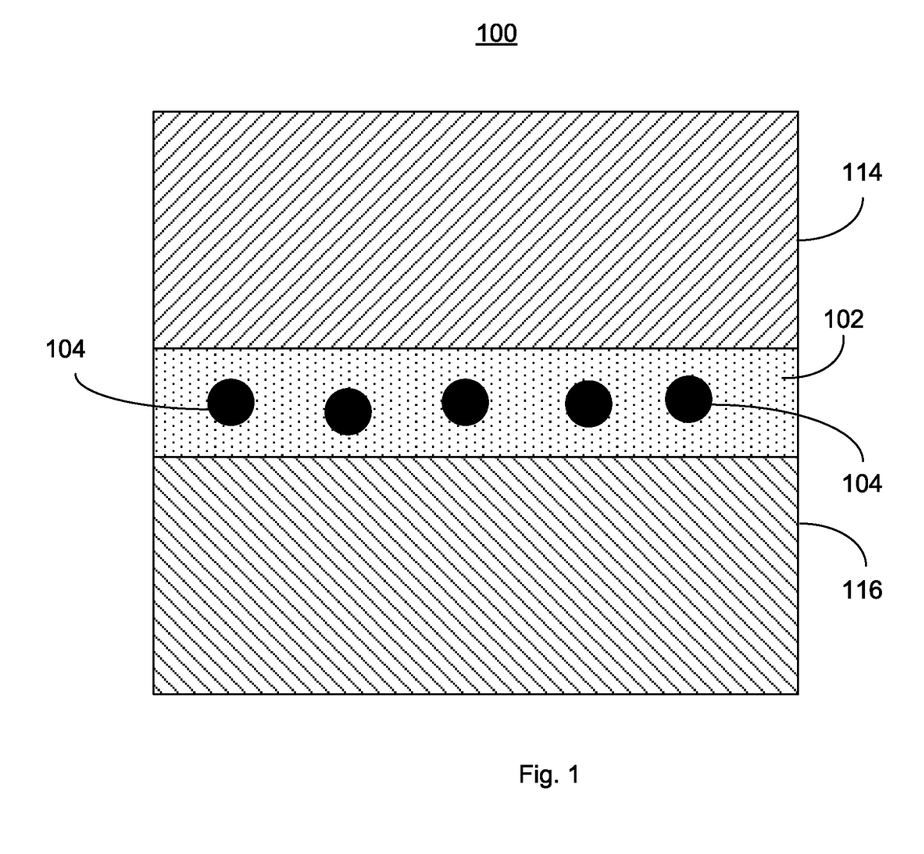
FIG. 1 is a cutaway view of a composite material in accordance with the current disclosure.

FIG. 1 illustrates a cutaway side view of a composite material 100 having an upper layer 114 and a lower layer 116 joined by an adhesive 102. The adhesive 102 may include wires 104. In an embodiment, the wires 104 are separate, that is, not intentionally connected although some overlap may occur. An orientation of the wires 104 is discussed more below with respect to FIG. 2, but as shown, the view is perpendicular to the axial direction of the plurality of wires 104. The upper and lower layers 114, 116 may be any of a number of known materials, including, but not limited to, plastics, fiberglass, or other non-ferrous materials. The adhesive may be an epoxy or other known adhesive.

Figure 2:
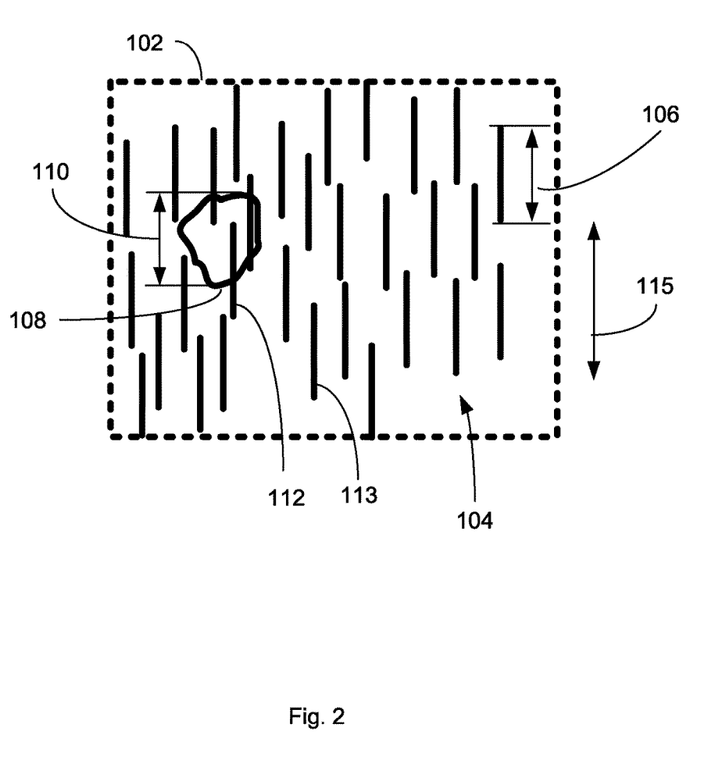
FIG. 2 is a cutaway top view of an embodiment of a layer of adhesive disposed in a composite material in accordance with the current disclosure.

FIG. 2 illustrates a cutaway top view of the adhesive 102 layer of the composite material 100 showing the plurality of wires 104. In this illustration, the adhesive 102 is depicted without the surrounding upper and lower layers 114, 116 of the composite material 100 for clarity. Each wire has a length 106. The length 106 may be selected to be in the same order of magnitude as a dimension 110 of a defect 108. As shown, a wire 112 may cross a boundary of the defect 108 and will have a different stress response profile from, for example, a wire 113 that is fully encapsulated and away from any defect. In an embodiment, it may be desirable to have the length of the wire 104 in a range of 80 to 120 times the diameter of the wire 104. The wires may be any of many known types of ferromagnetic wire, such as, but not limited to, alloys including HyMu "80"® an 80% nickel-iron-molybdenum alloy available from Carpenter Technology Corporation. The wires may also consist of other materials such as those in the developing area of ceramic magnetic compounds.

It should be noted that a known technique of mixing linear bodies (wires, fiberglass strands, etc.) into a compound and extruding the compound under pressure causes the linear bodies to align linearly as shown. While this process promotes linear alignment, it does not necessarily provide even spacing laterally or axially. The wires 104 are aligned in a first direction 115, referred to below in the discussion of FIG. 3.

Figure 3:
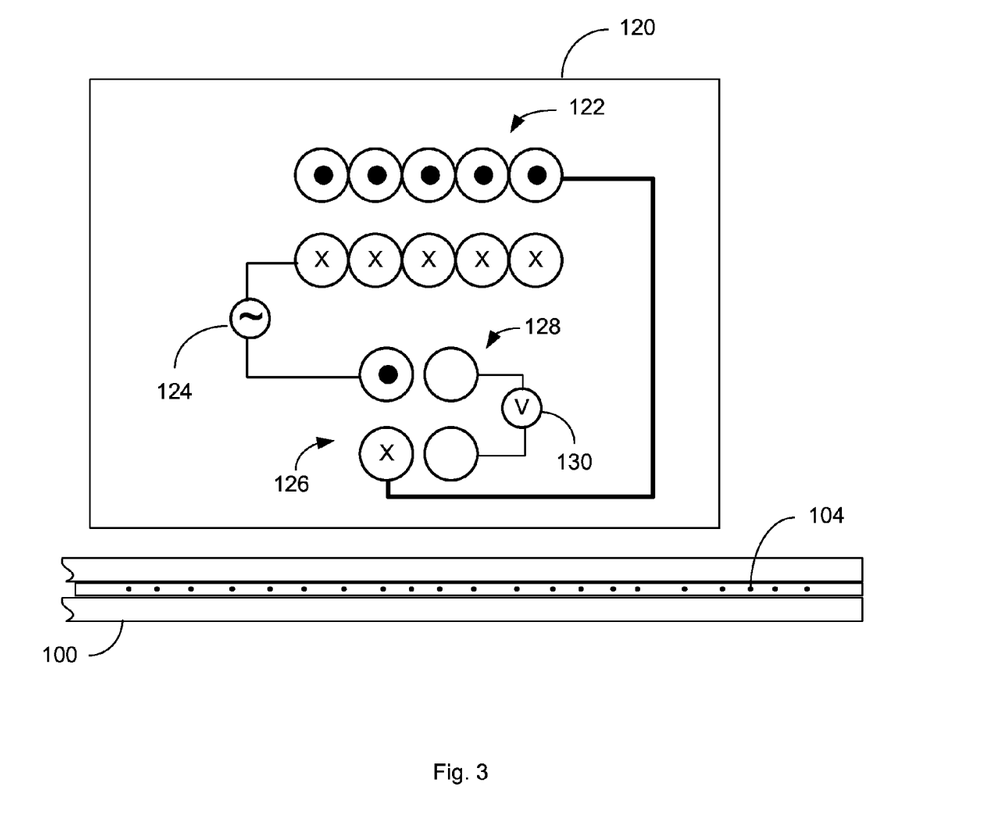
FIG. 3 is an illustration of a test apparatus for magnetic characterization of bonds in the composite material of FIG. 1.
Figure 4:
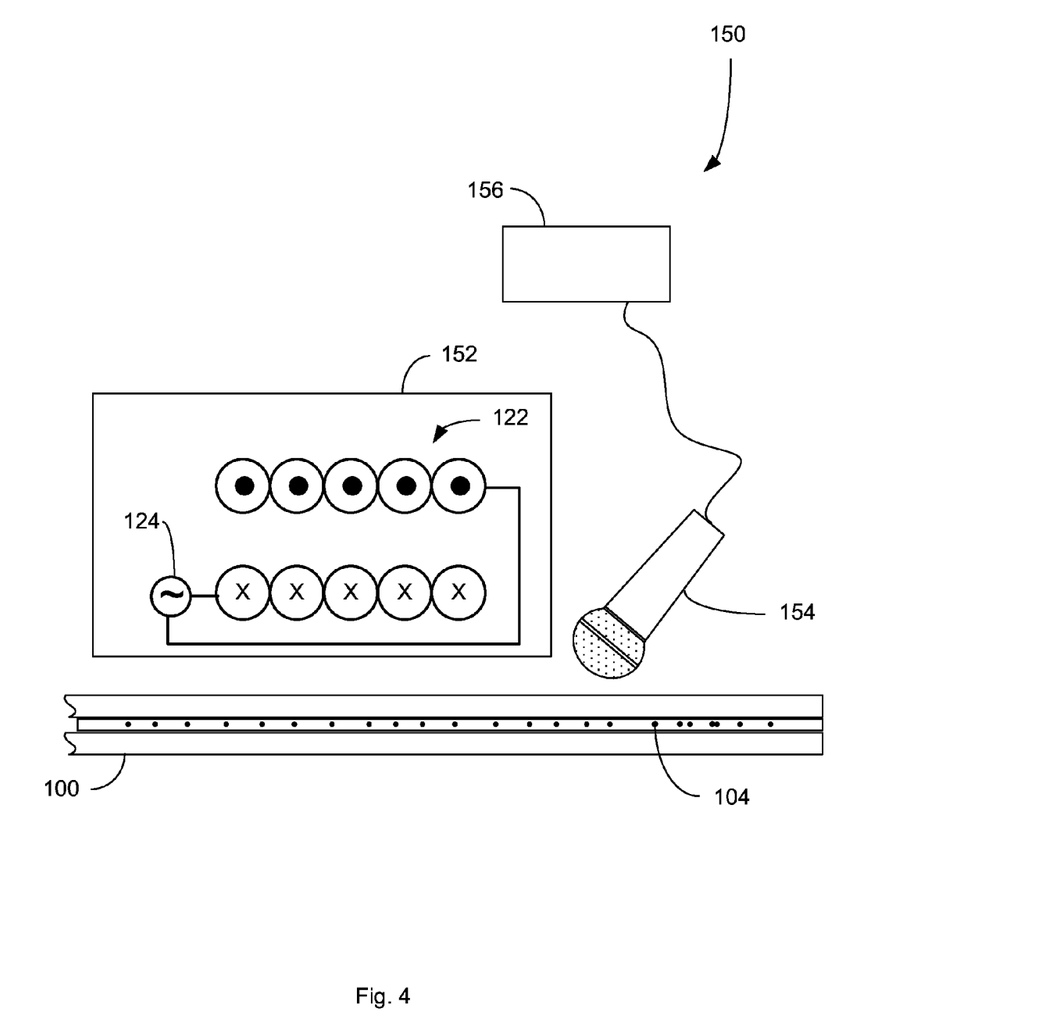
FIG. 4 is an illustration of another embodiment of a test apparatus for magnetic characterization of bonds in the composite material of FIG. 1.
Figure 5:
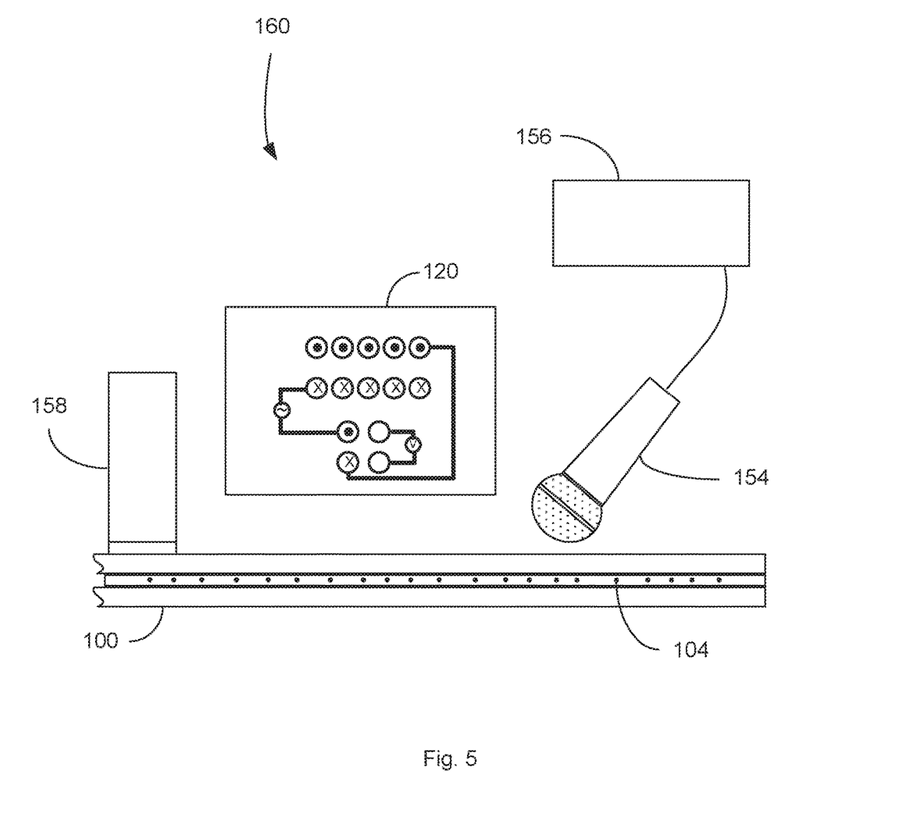
FIG. 5 is an illustration of yet another embodiment of a test apparatus for magnetic characterization of bonds in the composite material of FIG. 1.

FIGS. 3-5 illustrate various configurations of test environments. The wires 104 depicted in the composite material 100 are merely indicative of their presence and do not imply a particular orientation of the test apparatus with respect to an orientation of the wires 104.

FIG. 3 is an illustration of a test apparatus 120 for magnetic characterization of bonds in the composite material 100 of FIG. 2. The test apparatus 120 includes a magnetic field source 122 depicted as a coil of wire. The test apparatus 120 also includes a signal generator 124 for causing an alternating current in the magnetic field source 122. In an embodiment, the signal generator 124 may provide a sine wave in the audio range, for example, between 50 Hz and 20,000 Hz although frequencies above and below this exemplary range may be used. In another embodiment, the signal generator 124 may provide a signal between 900 Hz and 1100 Hz. The signal generator 124 may provide current at varying levels to provide different magnetic field strengths as needed during the testing process.

The test apparatus 120 may also include a detector coil 128 for detecting the magnetic field returned from the wires 104 of the composite material 100 responsive to the magnetic field source 122 and a meter 130. The meter 130 may be used for measuring a response signal generated by the detector coil 128. In an embodiment, the meter 130 may be, or may be attached to, a signal analyzer discussed in more detail below with respect to FIG. 4.

A compensation coil 126 may be used for self-calibration of the test apparatus 120. For example, prior to placing the test apparatus 120 near the composite material 100, the signal generator 124 may be activated to cause a magnetic field to be generated. A position of the compensation coil 126 relative to the detector coil 128 may be adjusted until there is no reading at the meter 130. Because the signal from the magnetic field source 122 is nulled out via this calibration process, the only signal at the detector coil 128 will be the response signal generated by the plurality of wires 104.

In an embodiment, the magnetic field generated by the magnetic field source 122 may be aligned predominantly in the first direction 115 of the wires 104. This allows the wires to magnetize more readily at lower fields strengths.

Turning to FIG. 4, an alternate embodiment of magnetic characterization of bond strength using a test apparatus 150 is illustrated. The test apparatus 150 includes source apparatus 152 with a magnetic field source 122 and a signal generator 124 as discussed above. A microphone 154 may be used to detect an audible response signal generated by magnetostriction of the wires in the composite material 100 responsive to a magnetic field provided by the magnetic field source 122. When using an audible response signal to find defects, it may be desirable to set the signal generator 124 to a frequency that corresponds to a responsive area within the microphone's frequency response curve. In an embodiment, the microphone 154 or a similar detector may be placed directly on a surface of the composite material 100. An analyzer 156 may be used to analyze the signal response from the microphone 154. The analyzer 156 may include a capability to perform a Fourier or similar transform on the response signal to characterize the response signal at fundamental and harmonic component frequencies.

Another embodiment of an apparatus 160 for magnetic characterization of bond strength is illustrated in FIG. 5. In this embodiment, the test apparatus 120 of FIG. 3 is used in conjunction with the microphone 154 of the embodiment of FIG. 4 so that both magnetic and acoustic response signals may be collected. In another variation of the above embodiments, a mechanical signal source 158 may be placed directly on the composite material 100. In an embodiment, the mechanical signal source 158 may be a piezo-electric device that operates well above the frequency of the magnetic field source 122. For example, the mechanical signal source may operate in a range of 100 kilohertz to 10 megahertz, although operational frequencies below 100 kilohertz and above 10 megahertz are possible. The mechanical signal source 158 sets up a mechanical signal in the form of a compression wave in the composite material 100 that creates additional stress on wires 104 that are near a void boundary, cross a void boundary, or are co-located at another defect. This additional stress accentuates the difference in response signals from well-formed bonds and those areas with defects.

FIGS. 6-11 illustrate exemplary results for magnetic characterization of bond strength. These exemplary results are from a controlled environment where a 6 mil (six thousandths of an inch) HyMu 80® ferro-magnetic wire 104 is subjected to varying levels of tensile stress and placed in a magnetic field of varying strengths. In the discussion that follows, the results discussed are similar for both magnetic response signals and acoustic response signals.

Figure 6:
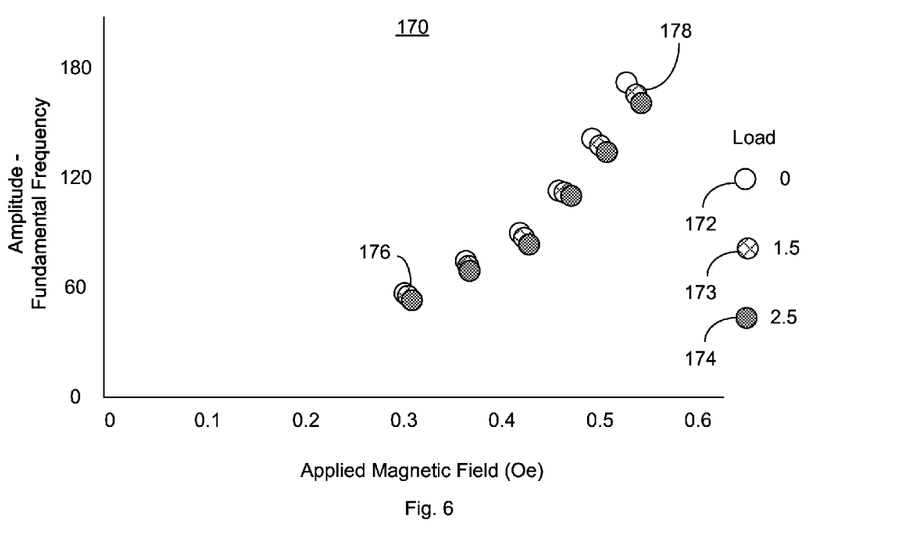
FIG. 6 is a chart illustrating a fundamental frequency amplitude of a response signal resulting from testing the composite material of FIG. 1.

FIG. 6 is a chart 170 that illustrates results for the wire 104 subjected to no load 172, a medium load (1.5 kilogram/mm$^2$) 173, and a high load (2.5 kilogram/mm$^2$) 174 at various field strengths. FIG. 6 shows the fundamental frequency response, that is, a response signal from the wire 104 at the same frequency as that of the magnetic field source 122. As can be seen, the response signals at 176 and 178 increase uniformly with increasing field strength. That is, the response signal of wires under no load 172 and the response signal of wires under a high load 174 are virtually identical.

Figure 7:
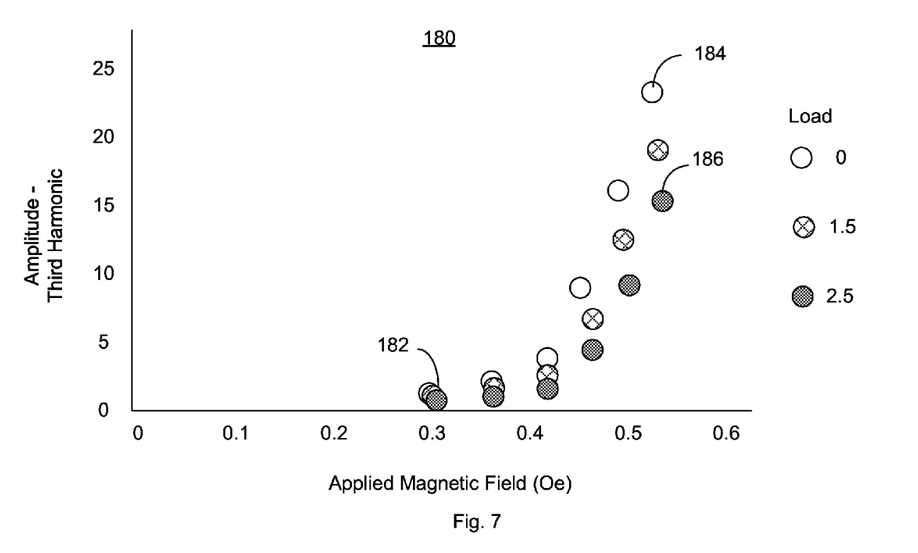
FIG. 7 is a chart illustrating a third harmonic amplitude of the response signal resulting from testing the composite material of FIG. 1.

However, the chart 180 of FIG. 7 illustrates that at low magnetic fields the stress responses at 182 are nearly the same while at high magnetic fields the high stress response 186 diverges significantly from the no load response 184.

Figure 8:
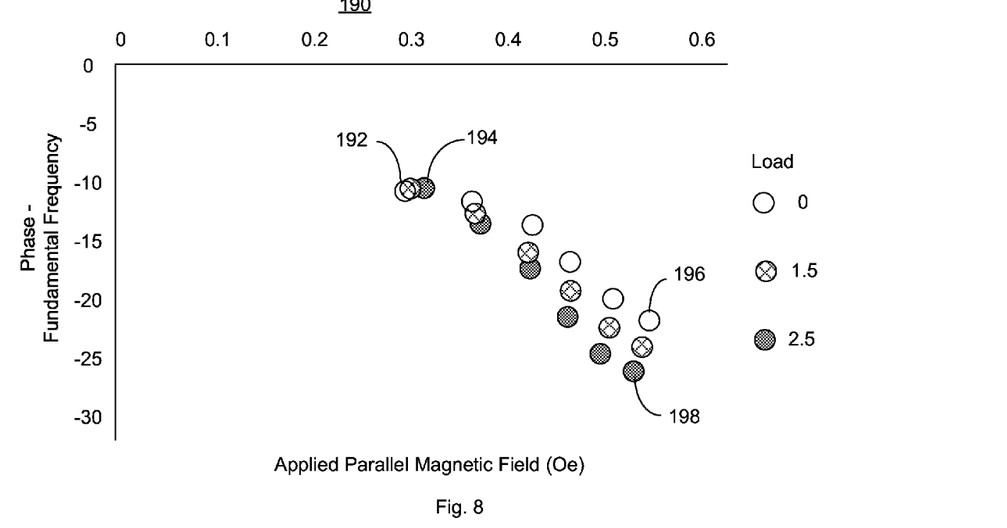
FIG. 8 is a chart illustrating a fundamental frequency phase of the response signal resulting from testing the composite material of FIG. 1.
Figure 9:
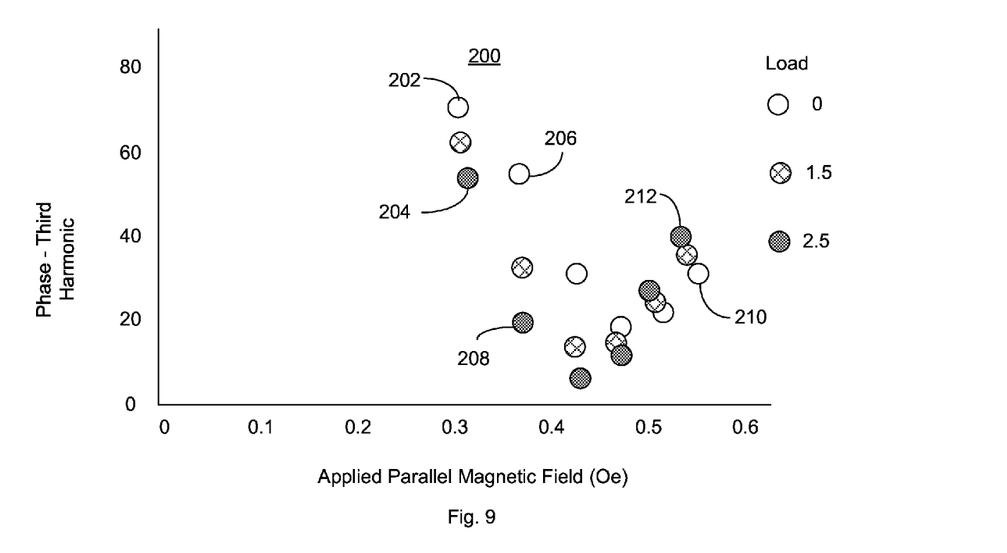
FIG. 9 is a chart illustrating a third harmonic phase of the response signal resulting from testing the composite material of FIG. 1.

Similarly, in FIG. 8 chart 190 illustrates that a phase response of the fundamental frequency has relatively close alignment between both the no-load response 192 and high load response 194 at low magnetic fields as well as at high magnetic fields, seen in response signals 196 and 198. As seen above however, the chart 200 of FIG. 9 shows that the third harmonic of the stress response signals diverge significantly at low magnetic field strengths with no-load response 202 and high-load response 204. An even greater divergence is shown between no-load 206 and high load 208 responses at an intermediate magnetic field strength. The response signals 210 and 212 at higher magnetic field strengths invert so that the no-load response 210 is below the high-load response 212 but do not diverge as much as the response signals at the lower magnetic field strengths.

Figure 10:
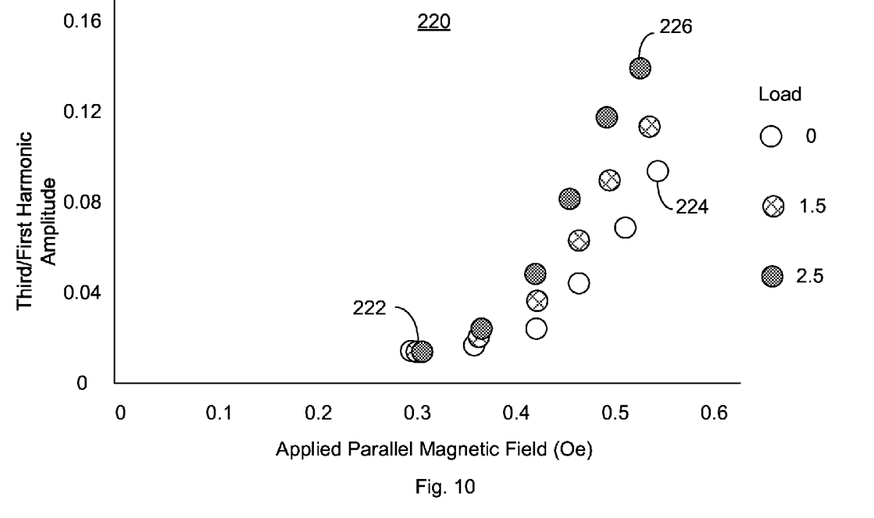
FIG. 10 is a chart illustrating a quotient of the third harmonic amplitude and the fundamental frequency amplitude of the response signal.
Figure 11:
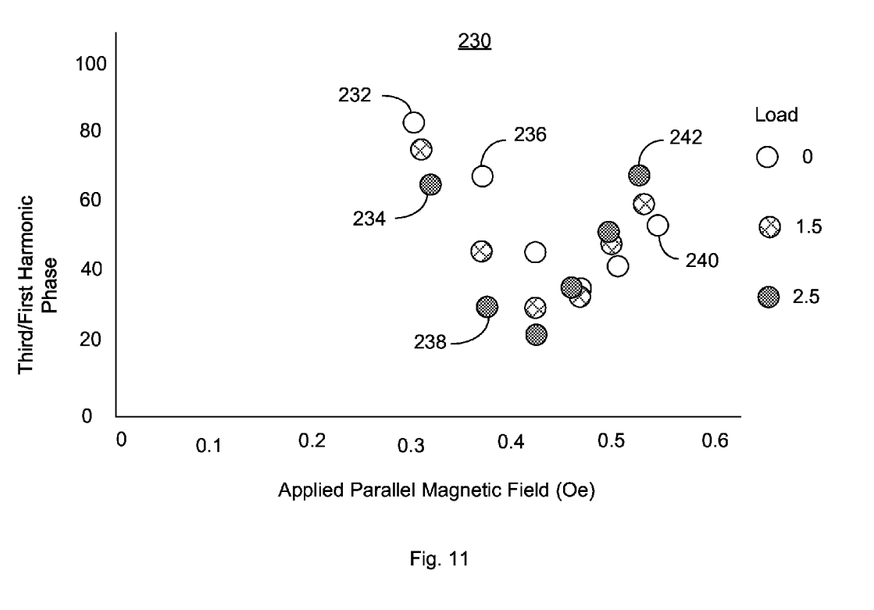
FIG. 11 is a chart illustrating a quotient of the third harmonic phase and the fundamental frequency phase of the response signal.

In order to characterize bond strength via magnetic response, it may be desirable to normalize the third harmonic signals to the fundamental frequency signals. FIG. 10 illustrates a chart 220 of such normalized values for response signal amplitudes. While the normalized values 222 at low magnetic field strengths are fairly consistent, the no load value 224 and high load value 226 diverge significantly at high magnetic fields. FIG. 11 illustrates normalized values for response signal phase in chart 230. In contrast to the chart 220 of FIG. 10, the values at lower magnetic fields 232, 234 and 236, 238 diverge while the values 240 and 242 are more correlated at higher magnetic field strengths. As shown, the amplitude or phase normalized responses, when taken separately or together show a significant divergence across the full range of magnetic field strengths. In extrapolating these results to the general testing environment, exposing a product under test to varying magnetic field strengths and plotting the results over a full surface area of the composite material reveals a sharp divergence between normalized response signals associated with defective areas of the product. Uniformly stressed wires 104 in well bonded areas provide response signals with a low divergence of amplitude and phase across a range of magnetic field strengths. However, in areas where a bonding defect occurs, wires at or in the vicinity of a defect will exhibit stress due to uneven curing of the adhesive 102 and their response signals will diverge from the normative response signals found elsewhere.

Even in a production item where a catastrophic bonding defect might occur such as one surface being largely contaminated, the normalized response signals from well bonded and defective areas will diverge even if the defective area is larger than the well-bonded areas so that the production unit will fail the testing process. Further, a product with a widespread defect may also fail either a non-destructive pull test or may fail an ultrasound test so that at least a combination of testing techniques may be useful to fully qualify a composite material 100.

The granularity of the magnetic test may be determined by the physical cross section of the magnetic field source 122. For example, in an embodiment, an area exposed to the magnetic field may be two to four times the area of an expected defect. In an embodiment, the area of a magnetic field developed by the magnetic field source 122 may be approximately one square inch. However, changes in detector sensitivity and characterization of defects in specific products may allow the area covered in a single test to be adjusted up or down accordingly.

Another aspect of using the third harmonic in signal processing response signals is that the magnetic field source 122 does not need to be in immediate proximity to the surface of the composite material being tested. In an embodiment, the test apparatus 120 may be 10 cm or more from the composite material 100 being tested. This offers flexibility in testing composites that may have features that hinder direct contact measurements, such as ultrasound.

An additional benefit to embedding wires 104, such as ferro-magnetic wires, is that inductive heating may be used to uniformly cure the adhesive 102 either in addition to, or in place of, normal external heating processes, e.g. baking.

Figure 12:
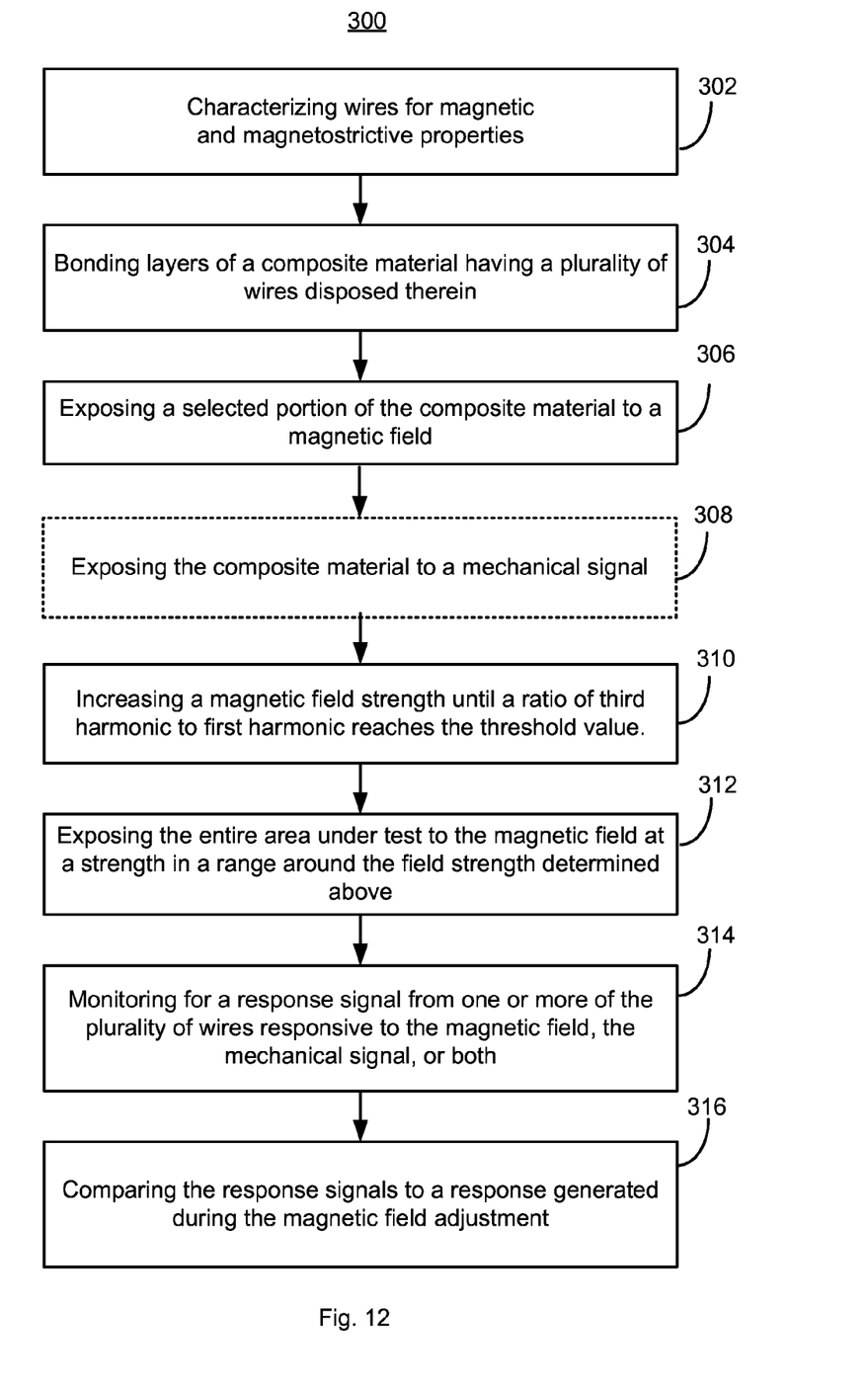
FIG. 12 is an illustration of operations performed by one embodiment of magnetic characterization of bond strength.

FIG. 12 is an illustration 300 of operations performed by one embodiment of characterization of bond strength. At block 302, wires may be characterized for magnetic field and magnetostrictive properties. For example, in a laboratory environment wire filaments may be subjected to tensile stress and subjected to magnetic fields of varying intensity. The resulting magnetic and audio response signals may be cataloged similar to the charts in FIGS. 6-9 for use in later testing of a composite material 100.

At block 304, layers of a composite material 100 may be bonded using an adhesive 102 with a plurality of wires 104 incorporated in the adhesive 102. Each of the plurality of wires may have a length in a same order of magnitude of a size of a defect being identified. In an embodiment, the composite material 100 may be provided separately from the testing process outlined in blocks 306-316.

At block 306, the composite material 100 may be exposed to a magnetic field. For example, a coil of wires may be energized with an alternating current to develop a magnetic field in the composite material 100. The test may be performed with an alternating magnetic field at a fixed frequency, for example, 1 kilohertz. Optionally, at block 308, the composite material 100 may be further exposed to a mechanical signal source 158, such as a piezo-electric device, that generates a compression wave in the composite material 100.

At block 310, a response signal from one or more the plurality of wires 104 may be monitored and used in a form of calibration beyond that of the field nulling process described above with respect to FIG. 3. Because each type of composite material 100 may be different, both in construction and thickness, various field strengths may be tested to determine an optimal range for the production product test. In this embodiment, a test apparatus, such as test apparatus 120, 150 or 160 may be positioned at one location of the composite material under test. A first field strength may be applied and allowed to stabilize and a figure of merit calculated for the response signal. In an embodiment, the figure of merit may be a quotient of the first and the third harmonic of the response signal. In other embodiments, other figures of merit may be used. If the figure of merit is well above or well below a desired value, such as 0.1 in one embodiment, the field strength may be increased or decreased as appropriate, in a step fashion, and the evaluation repeated. When the desired value of the figure of merit is reached, the corresponding field strength can be used as a center value for further testing of the full composite material 100. In an embodiment, this corresponding field strength may be the only value used during a test. In yet another embodiment, the figure of merit may be used for judging subsequent test result values. For example, if the desired figure of merit of 0.1 is developed at the calibration site, any value generated that is more than 15% from 0.1 may be regarded as a potential defect and more testing in that area may be performed.

At block 312, an entire area of the composite material under test may be scanned using the test apparatus 120, 150, 160. Based on the size of a test area of the test apparatus and the size of the composite material 100 to be tested, the test may be repeated at numerous locations of the composite material 100. The test may also be repeated at different magnetic field strengths, for example, in a range around the field strength found in the calibration discussed above.

The response signal may be monitored at block 314. In an embodiment, the response signal may be a magnetic response signal. In another embodiment, the response signal may be an acoustic signal. In analyzing the response signal, both an amplitude and a phase of the response signal may be used. In an embodiment, a third harmonic of the fundamental frequency of the response signal may be used to identify defective areas of the composite material 100. For example, a third harmonic amplitude response may be divided by the fundamental frequency amplitude response. The resulting normalized signal may be compared at block 316 to that resulting from the initial calibration area tested at block 310 and divergent signals may be used to identify potentially defective areas.

The ability to non-destructively test bond strength in composite materials 100 benefits both manufacturers and consumers of these composites. If, through such non-destructive testing, the use of mechanical through-fasteners can be eliminated, lighter and more complex composites can be developed and deployed. This affords greater flexibility in manufacturing, lower production costs, and lighter equipment. Equipment outfitted with such composite materials may be lighter, which often translates to more economic use, such as better fuel efficiency, benefiting end-users.

While only certain embodiments have been set forth, alternatives and modifications will be apparent from the above description to those skilled in the art. These and other alternatives are considered equivalents and within the spirit and scope of this disclosure and the appended claims.

What is claimed:

1. A method for non-destructive determination of an as-cured bond strength of a composite material that includes layers of material co-bonded with an adhesive incorporating a plurality of wires having a coercive force value, the method comprising:
    exposing the composite material to an alternating magnetic field having a field strength less than the coercive force value of the plurality of wires;
    monitoring for a response signal from one or more of the plurality of wires resulting from exposure to the alternating magnetic field; and
    determining a quality of the as-cured bond strength of the composite material based on a quotient of a third harmonic amplitude of the response signal and a fundamental frequency amplitude of the response signal.

2. The method of claim 1, further comprising exposing the composite material to a mechanical signal, wherein monitoring for the response signal from the one or more of the plurality of wires includes monitoring for the response signal from the plurality of wires responsive to the alternating magnetic field and the mechanical signal.

3. The method of claim 2, wherein a frequency of the mechanical signal is in a range from 100 kilohertz to 10 megahertz.

4. The method of claim 1, wherein each of the plurality of wires are aligned substantially parallel to each other in a first direction and wherein exposing the composite material to the alternating magnetic field comprises exposing the composite material to the alternating magnetic field with the alternating magnetic field aligned in the first direction.

5. The method of claim 1, further comprising calibrating a detector used to monitor for the response signal with a compensation coil.

6. The method of claim 1, further comprising calibrating a magnetic field strength for use in subsequent testing, wherein calibrating the magnetic field strength comprises successively increasing the magnetic field strength at a first area of the composite material until a desired figure of merit is reached.

7. The method of claim 1, wherein exposing the composite material to the alternating magnetic field comprises exposing the composite material to the alternating magnetic field having frequency of between 50 Hz and 20,000 Hz.

8. The method of claim 1, wherein exposing the composite material to the alternating magnetic field comprises applying an external alternating magnetic field at an area being inspected, the external alternating magnetic field applied at a fixed frequency and at several different amplitudes in a sequence.

9. The method of claim 1, further comprising determining a residual stress on at least one of the plurality of wires using the quotient of the third harmonic amplitude of the response signal and the fundamental frequency amplitude of the response signal.

10. The method of claim 9, wherein the response signal is a response magnetic field generated by the one or more of the plurality of wires responsive to the alternating magnetic field.

11. The method of claim 9, wherein the response signal is an acoustic response to the alternating magnetic field.

12. A test apparatus for non-destructive determination of an as-cured bond strength of a composite material that includes layers of material co-bonded with an adhesive, wherein the adhesive includes a plurality of wires having a coercive force value, the test apparatus comprising:
  a magnetic field source configured to cause an alternating magnetic field, the alternating magnetic field having a field strength less than coercive force value of the plurality of wires;
  a signal source positioned proximate the composite material, the signal source transmitting a primary signal into the composite material;
  a detector positioned proximate the composite material, wherein the detector receives magnetic and acoustic response signals generated by at least one wire of the plurality of wires responsive to the primary signal and the alternating magnetic field; and
  an analyzer that receives the magnetic and acoustic response signals and determines a presence of a defect in a bond between the adhesive and a layer of the composite material based on a characteristic of the magnetic and acoustic response signals.

13. The test apparatus of claim 12, wherein the signal source is mechanical signal source.

14. The test apparatus of claim 13, wherein the mechanical signal source operates at a frequency in a range of 100 kilohertz to 10 megahertz.

15. The test apparatus of claim 12, wherein the detector includes a compensation coil used to null out the primary signal.

16. The test apparatus of claim 15, wherein a position of the compensation coil is adjustable relative to the detector.

17. The test apparatus of claim 12, wherein the analyzer uses a ratio of an amplitude of a first harmonic of the response signal to another amplitude of a third harmonic of the response signals.

18. A method for non-destructive determination of an as-cured bond strength of a composite material that includes layers of material co-bonded with an adhesive incorporating a plurality of wires having a coercive force value, the method comprising:
  exposing the composite material to an alternating magnetic field of varying strength less than the coercive force value of the plurality of wires;
  applying a mechanical signal of varying load to the composite material;
  monitoring a response signal from one or more of the plurality of wires resulting from exposure to the alternating magnetic field and application of the mechanical signal;
  determining a location of a defect in the composite material based on a third harmonic phase response of the monitored response signal.

19. The method of claim 18, wherein determining the location of the defect in the composite material based on the third harmonic phase response of the monitored response signal comprises:
  determining the third harmonic phase response of the response signal; and
  normalizing the third harmonic phase response to a fundamental frequency signal.

20. The method of claim 19, wherein determining the location of the defect in the composite material based on the third harmonic phase response of the monitored response signal further comprises:
  determining a normalized response signal across the composite material; and
  detecting a divergence between the third harmonic phase response and the normalized response signal at the location of the defect.

21. The method of claim 18, wherein the response signal is an acoustic response to the alternating magnetic field.

* * * * *